United States Patent [19]

Kunii et al.

[11] 4,181,120
[45] Jan. 1, 1980

[54] VESSEL FOR ULTRASONIC SCANNER

[75] Inventors: Yutaka Kunii; Toshikuni Shimoji, both of Kawasaki, Japan

[73] Assignee: Tokyo Shibaura Electric Co., Ltd., Kawasaki, Japan

[21] Appl. No.: 789,745

[22] Filed: Apr. 21, 1977

[30] Foreign Application Priority Data

Apr. 23, 1976 [JP] Japan .................. 51-46154
Mar. 18, 1977 [JP] Japan .................. 52-30093

[51] Int. Cl.² ............................................. A61B 10/00
[52] U.S. Cl. ...................................... 128/660; 73/620
[58] Field of Search ............. 128/2.05 Z, 2 V, 24 A; 73/618-621, 632-633, 640, 641, 644, 67.8 S, 71.5 US, 622, 25, 31-33, 625

[56] References Cited

U.S. PATENT DOCUMENTS

| | | | |
|---|---|---|---|
| 2,943,297 | 6/1960 | Steinberger et al. | 340/9 |
| 3,310,977 | 3/1967 | McGaughey | 73/620 |
| 3,763,463 | 10/1973 | Muir | 340/1 R |
| 3,817,089 | 6/1974 | Eggleton et al. | 128/2.05 Z |
| 3,974,682 | 8/1976 | Soldner et al. | 128/2 V X |
| 4,034,744 | 7/1977 | Goldberg | 128/2 V |
| 4,058,114 | 11/1977 | Soldner | 128/2 V |
| 4,084,582 | 4/1978 | Nigam | 128/2 V |

FOREIGN PATENT DOCUMENTS 2414777 10/1975 Fed. Rep. of Germany .......... 128/2 V
260815 6/1970 U.S.S.R. .................................. 128/2 V

OTHER PUBLICATIONS

Lozovskii, B. V., "Modified Transducer for UTS Flow Detectors used to Examine Biological Objects", Biomed. Engng, vol. 6 #1, Jan.-Feb. 1972, pp. 48-49.

*Primary Examiner*—Robert W. Michell
*Assistant Examiner*—Francis J. Jaworski
*Attorney, Agent, or Firm*—Finnegan, Henderson, Farabow & Garrett

[57] ABSTRACT

A vessel for an ultrasonic scanner, comprising a protection cap and a vessel body; the protection cap including a window portion made of a material which is highly penetrable by ultrasonic energy and, a frame portion made of a material having a high absorption capacity for ultrasonic energy, and the vessel body having an opening sealed by the protection cap and housing an ultrasonic transmission medium and an ultrasonic probe. The vessel permits the ultrasonic probe to be positioned extremely close to the skin of the patient and the tomogram obtained by the ultrasonic apparatus is essentially free of disturbances caused by multiple reflections of the ultrasonic beam.

7 Claims, 6 Drawing Figures

VESSEL FOR ULTRASONIC SCANNER

BACKGROUND OF THE INVENTION

This invention relates to a vessel for housing an ultrasonic scanner of an ultrasonic diagnosis apparatus employing an immersion method and, in particular, pertains to a protection cap utilized with such vessel.

A tomogram of tissue of a living body can be obtained by irradiating the tissue with an ultrasonic wave. Differences in the structural composition of the tissue lead to differing attenuation of the ultrasonic wave. Thus, the tomogram may be obtained by utilizing the echo of the irradiated ultrasonic wave. Ultrasonic diagnosis systems based on this principle have been developed and applied to various medical fields.

Where an ultrasonic diagnosis apparatus is used for obtaining a tomogram of the heart, it is generally preferred to employ, a proximity scanning method so as to minimize the influence of the ribs and minimize multiple reflections of the ultrasonic beam. By "proximity scanning method" it is meant that an ultrasonic probe is settled extremely close to the skin of the patient so as to enable the ultrasonic beam to be scanned through the space between two adjacent ribs.

The ultrasonic beam can be scanned either through a linear scan path or through a sector scan. In a sector scan path the ultrasonic probe is moved so that the ultrasonic beam describes a circular sector. When it is intended to obtain a tomogram of the heart by the proximity scanning method which necessitates scanning the beam through the very small space between two adjacent ribs, the sector scan is very effective. In performing a sector scan, however, the ultrasonic probe should be positioned so as not to permit the tip thereof to contact the skin of the patient in the course of its scanning motion. Naturally the resultant obstruction of the scanning motion brings about a failure to obtain a uniform tomogram.

Appended FIG. 1 shows how to obtain a tomogram of the heart by a conventional proximity method. As shown in the drawing, an ultrasonic probe 3 is driven through a scanning path by a motor so that the scan motion is centered about a pivot shaft 0. Thus, the ultrasonic beam S emitted from the probe 3 to the heart 4 of a person receiving the ultrasonic diagnosis changes its direction of travel continuously. The ultrasonic beam irradiated to the heart 4 is reflected and received by the probe 3 which provides the basic input to the system which forms the tomogram of the heart.

In the prior art arrangement shown in FIG. 1, it is important to locate the ultrasonic probe 3 in an appropriate position. If the tip of the ultrasonic probe, i.e., the portion emitting and receiving the ultrasonic beam S, is positioned too far away from the skin 1 of the patient, the resultant tomogram of the heart 4 is influenced by the shadows cast by the ribs 2. The tomogram is also influenced in this case by multiple reflection of the ultrasonic beam. Naturally, it is preferred to position the ultrasonic probe 3 as close as possible to the skin 1 of the patient. However, if the probe 3 is positioned too close to the skin 1, there is a danger that the tip of the probe 3 could contact the skin 1 in the course of its scanning and the resultant interference with the scanning motion would destroy the uniformity of the ultimate tomogram.

In order to locate the ultrasonic probe in an optimum position, it is proposed to dispose the probe within a protection vessel. This method, however, has the drawback that multiple reflections of the ultrasonic beam would be; produced by interaction of the beam with the walls of the vessel. In addition, the ultrasonic beam would be attenuated within the vessel. Because of these drawback the resultant tomogram would be rendered unsatisfactory.

SUMMARY OF THE INVENTION

An object of this invention is to provide a vessel for an ultrasonic scanner permitting an ultrasonic probe to be positioned close to the skin of the patient while at the same time preventing the generation of multiple reflections of the ultrasonic beam.

Another object is to provide a cap for a vessel of the type described.

The vessel for an ultrasonic scanner according to this invention comprises a protection cap and a vessel body. The protection cap includes a window portion made of a material which is highly penetrable by ultrasonic wave energy and a frame portion made of a material having a high ultrasonic wave absorption capacity. The vessel body is further provided with an opening, which is sealed by the protection cap, and houses an ultrasonic transmission medium and an ultrasonic probe.

DETAILED DESCRIPTION OF PREFERRED EMBODIMENT

A vessel for an ultrasonic scanner according to this invention houses an ultrasonic transmission medium and an ultrasonic probe emitting the ultrasonic beam. The vessel is provided with an opening, which is sealed by a protection cap. It is convenient to explain first the protection cap which is a significant aspect of this invention.

The protection cap includes a window portion made of a material which is highly penetrable by ultrasonic energy and a frame portion made of a material having a high ultrasonic wave absorption capacity. The ultrasonic beam generated by the ultrasonic probe housed in the vessel is emitted and received through the window portion. In this case, multiple reflections of the ultrasonic beam are prevented because the portion of the beam irradiated to the frame portions of the vessel is absorbed thereby. The ultrasonic beam is thus reflected essentially only by the tissue area under examination, e.g., the heart, rendering it possible to obtain a greatly improved tomogram of that area.

The frame portion may be supported by a rigid material which has a low ultrasonic energy absorption capacity. Thus, such support material should not be disposed on the inner wall of the frame portion in order to prevent the irradiated ultrasonic beam from being reflected by the support members.

In general, a sheet of an elastic material such as rubber is readily penetrable by an ultrasonic beam and, thus, is suitable for use in forming the window portion, particularly where the sheet is sufficiently thin. An elastic material is also high in absorption capacity of an ultrasonic beam when used in sections or sheets which are reasonably thick. It follows that the window portion and the frame portion can thus be made of the same kind of elastic material, with the window portion being made thinner than the frame portion.

It is preferred that the window portion be outwardly curved, for example, be hemispherical in order to enable the clearance between the tip of the ultrasonic probe housed in the vessel and the window portion to be kept constant during the scanning motion of the probe. The protection cap described above is preferrably hermetically mounted to an open end of the vessel body which houses an ultrasonic transmission medium and an ultrasonic probe, as is described below for a preferred embodiment of the invention.

Figure 1:
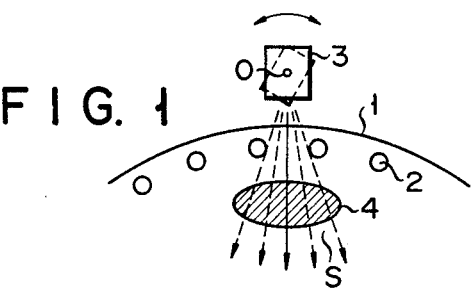
FIG. 1 is a diagram generally illustrating the proximity scanning method as carried out by a conventional ultrasonic diagnosis apparatus.
Figure 2A:
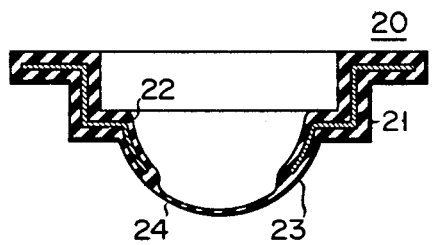
FIG. 2a is a cross sectional view of a protection cap according to this invention.
Figure 2B:
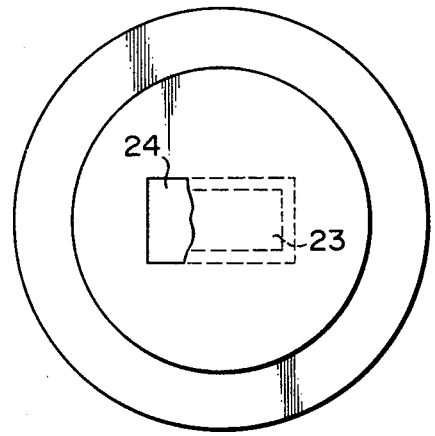
FIG. 2b is a plan view of the protection cap shown in FIG. 2a, FIG. 3a is a cross sectional view of a vessel for an ultrasonic scanner according to one embodiment of this invention.

FIGS. 2a, and 2b are a cross sectional view and a plan view, respectively, of the protection cap used in accordance with the invention. As shown in FIG. 2a, the protection cap 20 comprises a frame portion 23 and a window portion 24. The frame portion comprises an internal frame number 21 of a rigid reinforcing material such as a metal plate covered by an elastic film 22. The window portion 24 is formed of the same material as the film 22, but is much thinner in cross-sectional dimension. It is seen that the window portion and the frame portion adjacent to the window portion are designed to present jointly a hemispherical shape.

In operating the ultrasonic diagnosis apparatus, the window portion 24 is brought in direct contact with the skin of the patient. Thus, the thin film constituting the window portion is somewhat deformed. However, the window portion may be designed very small due to the narrow dimension, about 1 cm, of the ultrasonic beam emitted from the ultrasonic probe and the scanning angle of the probe. It follows that the deformation is so small that the tip of the ultrasonic probe is not brought in contact with the deformed window portion in the course of the scanning motion.

Where the protection cap is made of rubber with a metal plate used as the reinforcing material the window portion should preferably be as thin as possible and in general ranges from 0.1 to 0.5 mm thick, and the thickness of the rubber film coated on the inside surface of the metal plate should be 1 to 5 mm so as to permit sufficient absorption of the ultrasonic beam irradiated thereto. With this arrangement, the metal reinforcing plate may have a thickness of about 0.5 mm.

Figure 3A:
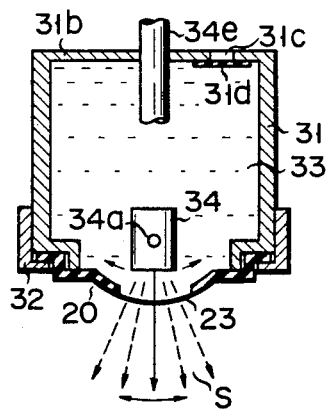
FIG. 3b is a cross sectional view of a vessel for an ultrasonic scanner according to another embodiment of this invention.
Figure 3B:
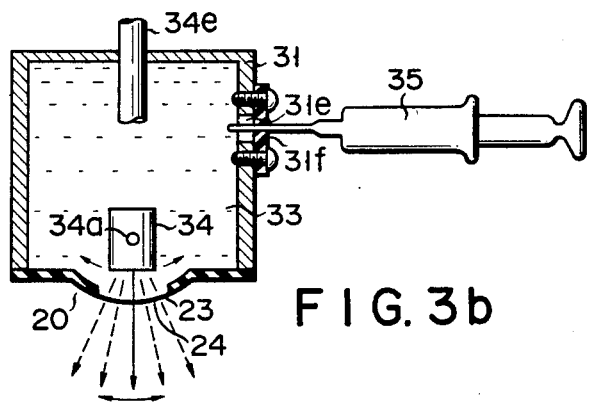

FIG. 3a shows the manner in which the protection cap 20 described above may be hermetically mounted to an open end of the cylindrical vessel body 31. In the embodiment shown, a metal ring 32 is used for clamping the cap 20 to the vessel and it may also be desirable to bond the cap 20 to the vessel body. Alternatively, the cap 20 may be formed integral with the vessel body 31 as shown in FIG. 3b.

The vessel body 31 is filled with a liquid substance acting as the transmission medium of the ultrasonic beam such as water, caster oil, or liquid paraffin. Further, the ultrasonic probe 34 fixed to a support shaft 34a is positioned such that the clearance between the tip of the probe 34 and the window portion 23 of the cap 20 remains constant during the scanning motion of the probe.

Figure 4:
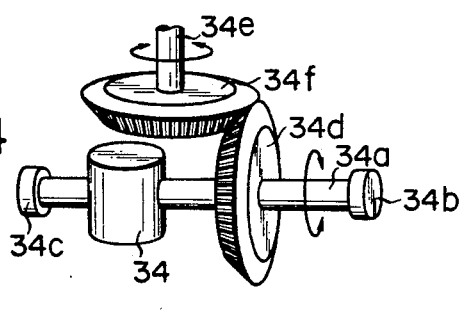
FIG. 4 is a perspective view showing one form of driving mechanism which may be employed to operate the ultrasonic probe according to this invention.

FIG. 4 shows one form of driving mechanism that may be used with ultrasonic probe 34. Bearings 34b and 34c are mounted to the inner wall of the vessel body 31 and serve to support the shaft 34a to which the probe 34 is fixed. A bevel gear 34d fixed to the shaft 34a is engaged with another bevel gear 34f mounted to the tip of a driving shaft 34e. As shown in FIG. 3a, the driving shaft 34e extends outside the vessel body 31 through a hole bored at the center of an upper wall 31b thereof. The driving shaft 34e is rotated in clockwise and anti-clockwise directions alternately by a motor or the like (not shown). This particular motion is transmitted to the support shaft 34a through the bevel gears 34f and 34d, producing a sector scanning motion of the ultrasonic probe 34. The ultrasonic beam S emitted from the probe 34 is scanned through a sector centered about shaft 34a.

In carrying out an ultrasonic diagnosis with the apparatus described, the protection cap 20 of the vessel is disposed on the skin of the patient. Thus, the window portion 24 of the cap, which is made of a highly elastic thin film, is pushed upward to some extent in some cases. In this case, the pressure of the liquid is increased within the vessel, giving rise to the problem of liquid leakage from the sealing portion of the vessel. To prevent this problem, a hole 31c is bored through, for example, the upper wall 31b of the vessel body 31. An elastic thin film 31d made of rubber or the like is stretched to seal the inner end of the hole 31c as shown in FIG. 3a. In this case, the thin film 31d is pushed upward, thereby preventing any substantial increase in the pressure applied to the walls of the vessel by the liquid transmission medium. This minimizes the leakage problem.

It should also be noted that the liquid housed in the vessel gradually permeates through the window portion 24 of the protection cap. This gradually decreases the liquid pressure within the vessel, resulting in a greater inward deformation of window portion 24 when it is applied to the skin of the patient. In some cases, this may lead to the tip of the ultrasonic probe 34 actually coming in contact with the window portion, resulting in obstruction of the head-scanning motion. Also, the window portion of the protection cap may fail to make good, uniform contact with the skin of the patient, giving rise to multiple reflections of the ultrasonic beam. In order to prevent these problems, it is necessary to periodically replenish the supply of liquid in the vessel.

FIG. 3b shows a vessel equipped with a liquid replenishing means. As shown in the drawing, a hole 31e is bored through, for example, a side wall of the vessel body 31. A lid 31f made of a soft material such as rubber or cork is fitted to the hole 31e by screws or adhesives so as to seal the hole 31e. When a large amount of liquid is introduced into the vessel, the lid 31f is taken away. On the other hand, the needle of a syringe 35 is pierced through the lid 31f when only small quantities of liquid are required to be supplied to the vessel for the purpose of maintaining a predetermined liquid pressure within the vessel. Naturally, the needle of the syringe is withdrawn after the desired amount of liquid has been injected. In this case, the small hole formed in the lid 31f by the needle immediately disappears because the lid is made of a soft material. Clearly, the vessel is kept airtight and the liquid housed in the vessel does not leak from the vessel.

As has been described in detail, the open end of the vessel body 31 is sealed by a protection cap. Where the frame portion of the protection cap is reinforced by a rigid material, the cap is free from deformation. Thus, the clearance between the tip of the ultrasonic probe and the inner face of the protection cap is kept substantially constant even when the vessel is disposed on the skin of the patient. This permits disposing the ultrasonic probe extremely close to the inner face of the cap. Accordingly the tip of the probe is positioned satisfactorily close to the skin of the patient for operating the ultrasonic diagnosis apparatus. The ultrasonic beam is transmitted and received without experiencing the multiple reflection problem.

It is also important to note that the ultrasonic beam is transmitted and received through the window portion made of a material which is readily penetrable by the ultrasonic beam. Thus, attenuation of the ultrasonic beam is negligible when the beam passes through the window portion of the cap. On the other hand, the ultrasonic beam hitting the inner wall of the frame portion of the protection cap is substantially fully absorbed because the inner wall is made of material having a high ultrasonic absorption capacity. The particular protection cap provided in accordance with the invention thus enables the production of tomographs free from disturbance of multiple beam reflections. An additional advantage to be noted is that because the protection cap is made of or covered with an elastic material, it can be mounted to the vessel body without the use of a special packing material.

As described in detail, the vessel for an ultrasonic scanner according to this invention permits an ultrasonic probe to be positioned extremely close to the skin of the patient. In addition, the tomogram obtained by the ultrasonic diagnosis is rendered free from disturbance by multiple reflections of the ultrasonic beam.

What is claimed is:

1. An ultrasonic sector scanner for an ultrasonic diagnosis apparatus comprising:
    a vessel body containing an ultrasonic transmission medium;
    a protection cap made of an elastic material forming a wall of said vessel, said protection cap including a frame portion comprising a relatively thick section of elastic material with a rigid inner member imbedded therein such that said frame portion has reinforcing characteristics and a high ultrasonic energy absorption capacity, and a thin elastic window portion readily penetrable by ultrasonic energy, a section of said frame portion and said window portion being configured to form an outward projection in said vessel wall having a substantially semicircular cross-section which retains substantially the same shape when brought into contact with the skin of a patient due to the reinforcing characteristics of the frame portion of said projection;
    an ultrasonic probe for transmitting and receiving an ultrasonic beam, said ultrasonic probe being supported within said body and immersed in said medium such that the transmitting and receiving elements of said probe are positioned in proximity to the inner surface of said projection; and
    means for pivoting said ultrasonic probe relative to said protection cap through a predetermined sector scan angle such that said transmitting and receiving elements of said probe are moved in a scan path substantially parallel to the semicircular contour of said projection, whereby the section of said vessel wall including said projection is adapted to be pressed against the skin of a patient to position said ultrasonic probe in close proximity to the tissue areas of said patient to be diagnosed.

2. The ultrasonic sector scanner set forth in claim 1 wherein the shape of said projection is determined by the width of said ultrasonic beam and said predetermined sector scan angle.

3. The ultrasonic sector scanner set forth in claim 1 wherein the clearance between said ultrasonic probe and the inner surface of said projection is substantially smaller than the maximum depth diagnosable by said ultrasonic diagnosis apparatus.

4. The ultrasonic sector scanner according to claim 1, wherein said protection cap is formed integral with said vessel body.

5. The ultrasonic sector scanner according to claim 1, wherein said vessel body is provided with a hole sealed with an elastic film for adjusting the internal pressure of said vessel.

6. The ultrasonic sector scanner according to claim 1, wherein the vessel body is provided with a hole for injecting said ultrasonic transmission medium, said hole being normally closed by a lid made of a soft material.

7. The ultrasonic sector scanner according to claim 1, wherein said elastic material is rubber.

* * * * *

UNITED STATES PATENT AND TRADEMARK OFFICE
CERTIFICATE OF CORRECTION

PATENT NO. : 4,181,120
DATED : January 1, 1980
INVENTOR(S) : Yutaka Kunii and Toshikuni Shimoji It is certified that error appears in the above-identified patent and that said Letters Patent are hereby corrected as shown below:

First page, in the abstract, line 11:

Insert --diagnosis-- between "ultrasonic" and "apparatus".

Column 5, line 49:

Insert --core-- between "inner" and "member".

Signed and Sealed this

Twenty-fifth Day of March 1980

[SEAL]

Attest:

SIDNEY A. DIAMOND

Attesting Officer      Commissioner of Patents and Trademarks